United States Patent
Chang et al.

(10) Patent No.: US 9,053,907 B2
(45) Date of Patent: Jun. 9, 2015

(54) SYSTEM AND METHOD OF ION NEUTRALIZATION WITH MULTIPLE-ZONED PLASMA FLOOD GUN

(75) Inventors: Chun-Lin Chang, Jhubei (TW); Chih-Hong Hwang, New Taipei (TW); Wen-Yu Ku, Hsinchu (TW); Chi-Ming Yang, Hsinchu (TW); Chin-Hsiang Lin, Hsin-Chu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 166 days.

(21) Appl. No.: 13/439,124

(22) Filed: Apr. 4, 2012

(65) Prior Publication Data
US 2013/0264498 A1 Oct. 10, 2013

(51) Int. Cl.
*A61N 5/00* (2006.01)
*G21G 5/00* (2006.01)
*H01J 37/317* (2006.01)
*G21K 1/14* (2006.01)

(52) U.S. Cl.
CPC .............. *H01J 37/3171* (2013.01); *A61N 5/00* (2013.01); *G21G 5/00* (2013.01); *G21K 1/14* (2013.01); *H01J 2237/0044* (2013.01)
USPC ................... 250/492.1; 250/492.21; 250/251; 250/397; 250/423 R

(58) Field of Classification Search
USPC .............. 250/492.1, 492.21, 251, 397, 423 R
See application file for complete search history.

(56) References Cited

U.S. PATENT DOCUMENTS

| 4,786,814 | A | 11/1988 | Kolondra et al. |
| 5,399,871 | A | 3/1995 | Ito et al. |
| 5,777,209 | A | 7/1998 | Tien |
| 6,359,286 | B1 | 3/2002 | Ito et al. |
| 2001/0013578 | A1 | 8/2001 | Seki et al. |
| 2003/0183780 | A1* | 10/2003 | Sano et al. ............... 250/492.21 |
| 2006/0113492 | A1* | 6/2006 | Kawaguchi et al. ...... 250/492.21 |
| 2007/0228294 | A1* | 10/2007 | Ito et al. .................. 250/492.21 |

FOREIGN PATENT DOCUMENTS

| JP | 05-054847 | | 3/1993 |
| JP | 8-21361 | B2 * | 3/1996 |
| KR | 2004-0049416 | | 6/2004 |
| KR | 2004-0055722 | | 6/2004 |
| WO | 02/43104 | A2 | 5/2002 |
| WO | 2005/117059 | A1 | 8/2005 |

OTHER PUBLICATIONS

Kurunczi, P.F. et al., "Advanced Charge Control for Single Wafer Implanters", CP866, Ion Implantation Technology, edited by Kirkby, K.J. et al., American Institute of Physics, 2006, pp. 445-448.

(Continued)

*Primary Examiner* — Nikita Wells
*Assistant Examiner* — Meenakshi Sahu
(74) *Attorney, Agent, or Firm* — Duane Morris LLP

(57) ABSTRACT

An apparatus comprises a plasma flood gun for neutralizing a positive charge buildup on a semiconductor wafer during a process of ion implantation using an ion beam. The plasma flood gun comprises more than two arc chambers, wherein each arc chamber is configured to generate and release electrons into the ion beam in a respective zone adjacent to the semiconductor wafer.

18 Claims, 6 Drawing Sheets

(56) References Cited

OTHER PUBLICATIONS

Radovanov, S. et al., "In Situ Charging Potential Monitoring for a High Current Ribbon Beam", Conference on Ion Implantation Technology, 2000, pp. 577-580.

Wan, Z. et al., "Water Cooled Plasma Flood Source for Intense Ion Beam Implantation", Proceedings of the 14th International Conference on Ion Implantation Technology, Sep. 2002, pp. 432-435.

Official Action issued Nov. 22, 2013 in counterpart Korean Patent Application No. 10-2012-0085672, with English translation.

Official Action issued Nov. 22, 2013 in counterpart Korean Patent Application No.10-2012-0085672, with English translation.

Official Action issued Jul. 11, 2014 in counterpart Taiwan Patent Application.

\* cited by examiner

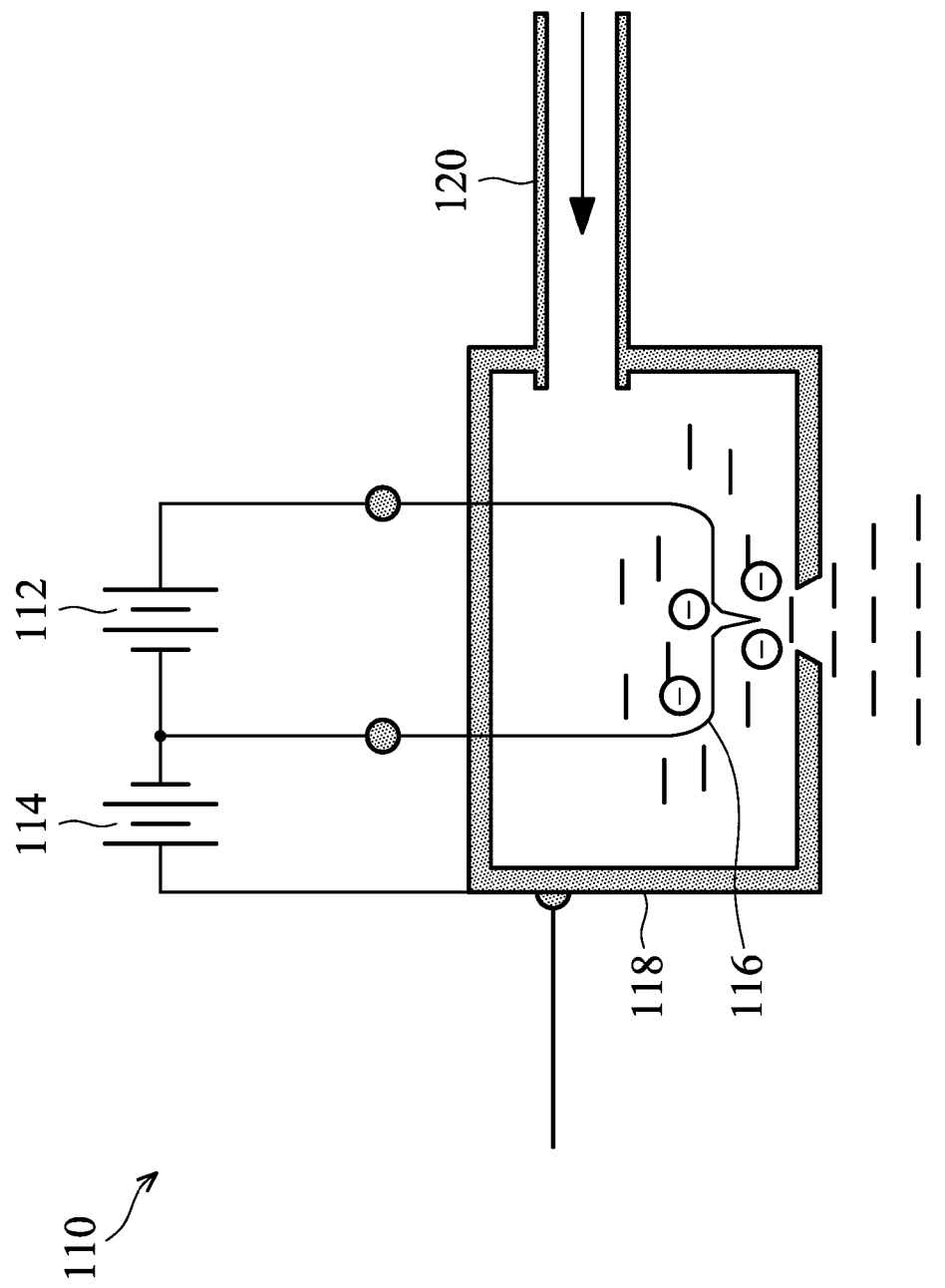

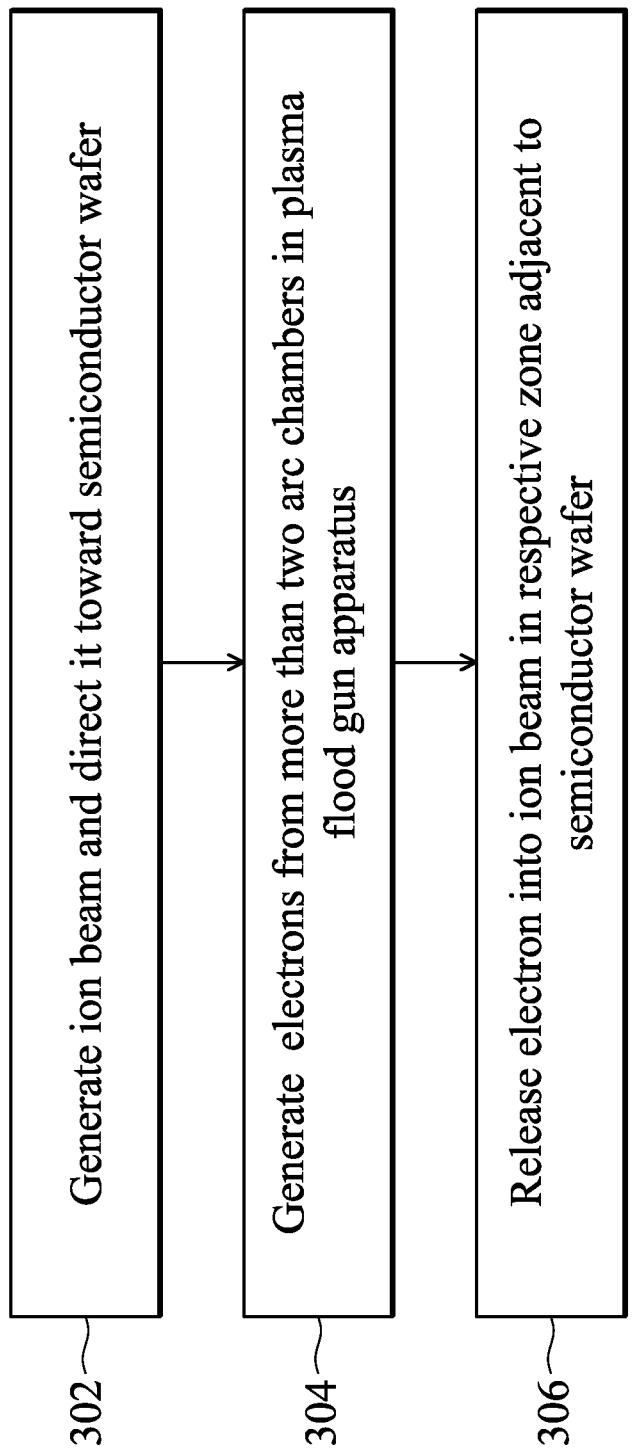

SYSTEM AND METHOD OF ION NEUTRALIZATION WITH MULTIPLE-ZONED PLASMA FLOOD GUN

FIELD

The disclosed system and method relate to semiconductor processing. More particularly, the disclosed subject matter relates to a plasma flood system for use in ion implantation equipment in the process of doping semiconductors.

BACKGROUND

Ion implantation is commonly used for doping a semiconductor material at precisely controlled depths and dopant concentrations. An ion implanter generally includes an ion source to generate an ion beam, ion beam transport optics for accelerating the ion beam, and a process chamber where the ion implantation on a semiconductor wafer occurs. The ions are mostly positively charged.

During ion implantation, the charged ion beam produces a build-up of charges on the surface of the semiconductor wafers in the process chamber. The surfaces of semiconductor wafers are generally insulating or semi-conductive. Such a charge build-up interferes with automatic wafer handling, and the implantation process itself; resulting in reduction in within-wafer uniformity (WiWU) and ultimately reduction in wafer yield.

Meanwhile, the size of semiconductor wafers has gradually increased to improve throughput and reduce cost per die. For example, in the transition from 300 mm to 450 mm wafer size, the wafer area increases by 125%. The within wafer uniformity (WiWU) becomes more difficult to maintain in the more-than-double-sized wafer.

In an ion implantation system, a plasma flood gun or system is used in front of a wafer. The plasma flood gun generates and releases electrons. These electrons neutralize the positive charged ion beam before the ion beam strikes the wafer's surface.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like numerals denote like features throughout specification and drawing.

FIG. 1C is an enlarged detail of an exemplary arc chamber in the plasma flood gun in FIG. 1A and 1B.

FIG. 3 is a flow chart diagram illustrating an ion implantation method comprising steps of generating and releasing electrons from more than two arc chambers in a plasma flood gun apparatus, into the ion beam, in accordance with some embodiments.

DETAILED DESCRIPTION

Figure 1A:
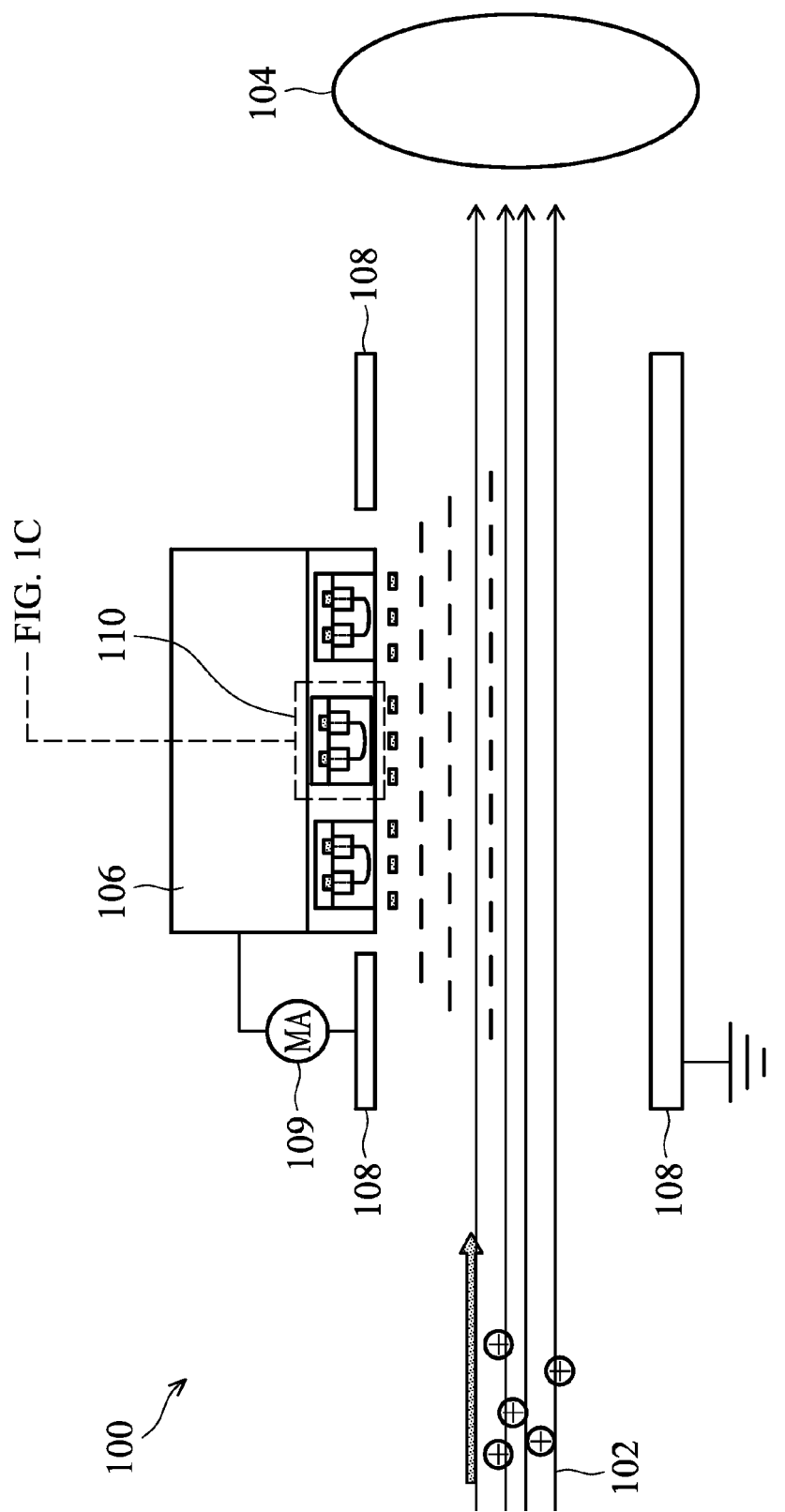
FIG. 1A illustrates an exemplary system of ion implantation having a plasma flood gun comprising more than two arc chambers, which are oriented in a direction parallel to the ion beam direction, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In an ion implantation process, the charge buildup on the wafers becomes more significant when the wafer size increases. For example, compared to that for the 300 mm wafers, a higher ion beam current is used to increase productivity in an ion implantation platform for the 450 mm wafers. So the charge buildup on the 450 mm wafers increases.

The inventors have determined that charge buildup is a key contributor to within wafer non-uniformity. So it is important to reduce such positive charge buildup on the wafer surface.

An apparatus having a plasma flood gun comprising more than two arc chambers, a related ion implantation equipment system and an ion implantation method are provided to neutralize a positive charge buildup on a semiconductor wafer during a process of ion implantation using an ion beam.

In some embodiments, the apparatus comprises a plasma flood gun, which comprises more than two arc chambers. Each arc chamber is configured to generate and release electrons into the ion beam in a respective zone adjacent to the semiconductor wafer.

In some embodiments, the more than two arc chambers in the apparatus are oriented in a direction parallel to the direction of the ion beam. In some other embodiments, the more than two arc chambers are oriented at an angle with respect to the direction of the ion beam. In some embodiments, this angle is 90 degrees, for example.

In some embodiments, the more than two arc chambers are also arranged in a configuration selected from a group consisting of a straight line, two parallel lines, a rectangle, a square, a triangle and a ring shape.

In some embodiments, the more than two arc chambers are configured in any three dimensional positional combinations of direction and shape.

In some embodiments, an ion implantation equipment system comprises
an ion beam source; and
a plasma flood gun apparatus for neutralizing a positive charge buildup on a semiconductor wafer during a process of ion implantation using an ion beam. The plasma gun apparatus comprises:
more than two arc chambers, wherein each arc chamber is configured to generate and release secondary electrons into the ion beam in a respective zone adjacent to the semiconductor wafer.

In some embodiments, an ion implantation method comprises the steps of generating an ion beam and directing the ion beam toward a semiconductor wafer;

generating secondary electrons from more than two arc chambers in a plasma flood gun apparatus; and releasing the secondary electrons into the ion beam adjacent to the semiconductor wafer. The secondary electrons neutralize the ion beam adjacent to the semiconductor wafer, mitigate or eliminate the charge buildup on the semiconductor wafer.

FIG. 1A illustrates an exemplary system of ion implantation having a plasma flood gun comprising more than two arc chambers, which are oriented in a direction parallel to the ion beam direction, in accordance with some embodiments. FIG. 1A is a schematic side-view of a portion of an ion implantation equipment system 100 according to the disclosure.

The system 100 comprises an ion source providing an ion beam 102, and a plasma flood gun 106, which comprises more than two arc chambers 110.

The ion source providing ion beam 102 has functions of generating an ion beam, accelerating and directing the ion beam to a semiconductor wafer 104, which is doped by ion beam 102. The ion source also includes a mass separator which generates a magnetic field to separate other ions from the desired ions in ion beam 102.

Ion beam 102 is positively charged in some embodiments. It is in the form of a certain shape according to a cross-section view. For example, in some embodiments such shape is a rectangle or ellipse.

Semiconductor wafer 104 is any wafer of any semiconductor materials such as silicon or III-V semiconductor compounds. Semiconductor wafer 104 is fixed on a holder in a semiconductor processing chamber. For example, in some embodiments, wafer 104 is held by an electrostatic chuck.

Plasma flood gun 106 comprises more than two arc chambers 110. Electrons are generated inside each arc chamber 110, and released through at least one aperture on one wall of arc chamber 110 into ion beam 102. The negative signs (−) in all the drawings represent electrons. In some embodiments, the electrons are secondary electrons. An exemplary arc chamber 110 is described in details hereafter in the related structures shown in FIG. 1C.

In some embodiments, the more than two arc chambers 110 in the exemplary plasma flood gun 106 are oriented in a direction parallel to the direction of the ion beam 102, as shown in FIG. 1A. These arc chambers release electrons into ion beam 102 in a respective zone adjacent to semiconductor wafer 104. In some embodiments, the released electrons are secondary electrons, and ion beam 102 is positively charged. The secondary electrons neutralize ion beam 102 adjacent to semiconductor wafer 104, and reduce or eliminate any possible charge buildup on the surface of semiconductor wafer 104.

Plasma flood gun 106 is also connected with a cage 108, and an emission current monitor 109. In some embodiments, cage 108 has at least two walls which are interconnected with each other, and at least one of the walls is grounded.

In some embodiments, emission current monitor 109 is used to monitor the currents in each arc chambers, and also adjust the rate and concentration of the electrons released from each arc chamber to a respective zone adjacent to semiconductor wafer 104.

For brevity, such plasma food gun comprising more than two arc chambers is also called a "multiple-zoned" plasma food gun.

Figure 1B:
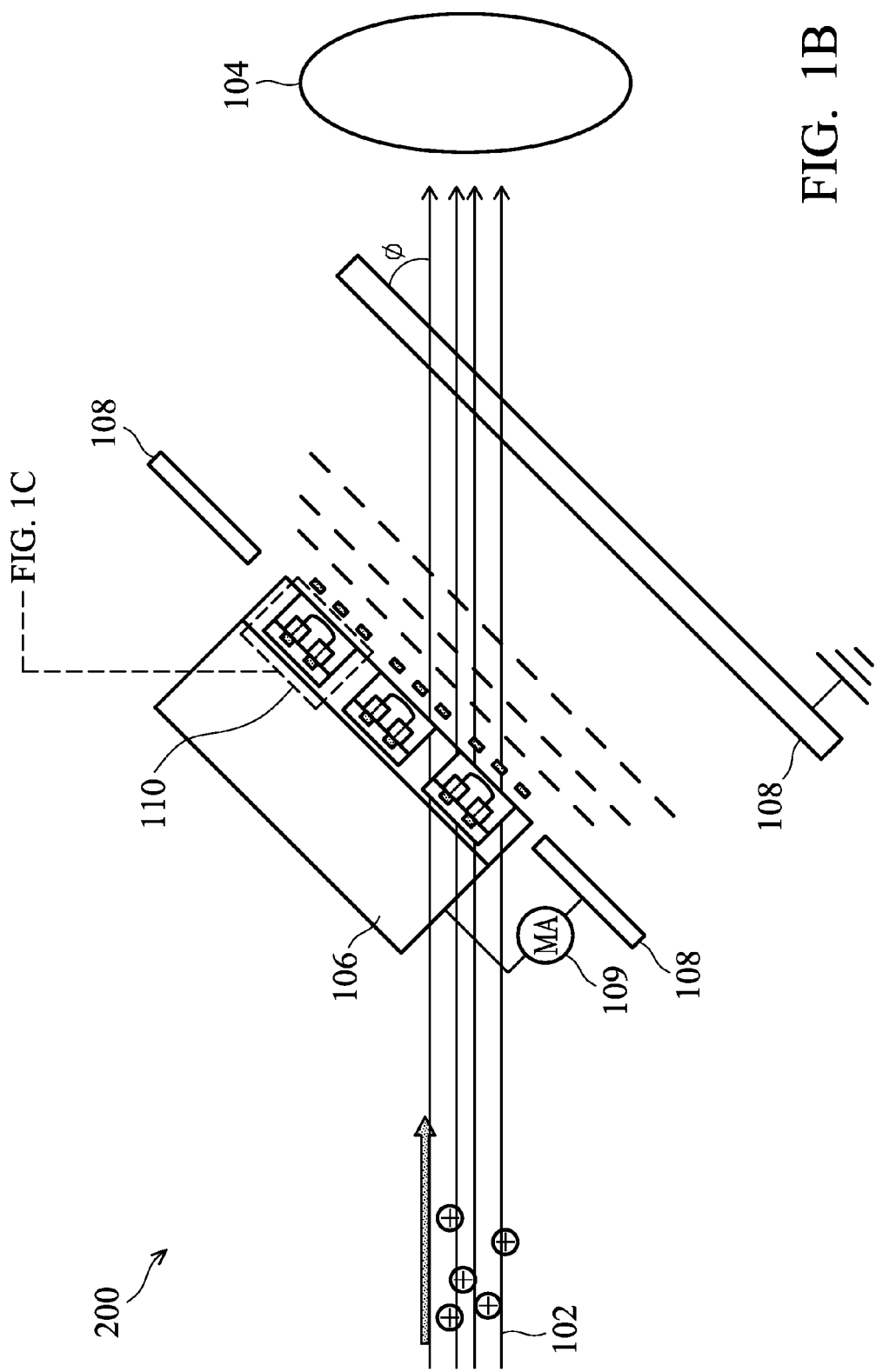
FIG. 1B illustrates an exemplary system of ion implantation having a plasma flood gun comprising more than two arc chambers, which are oriented at an angle with respect to the ion beam direction, in accordance with some embodiments.

FIG. 1B illustrates an exemplary system of ion implantation 200 having a plasma flood gun comprising more than two arc chambers, which are oriented at an angle with respect to the ion beam direction, in accordance with some embodiments. In FIG. 1B, like items are indicated by like reference numerals, and for brevity, descriptions of the structure, provided above with reference to FIG. 1A, are not repeated.

The exemplary system of ion implantation 200 in FIG. 1B is similar to that in FIG. 1A, except that the flood plasma gun 106 comprising more than two arc chambers 110 is oriented at an angle with respect to the direction of ion beam 102. In some embodiments, the more than two arc chambers 110 are orientated in a plane, which is at an angle with respect to the direction of ion beam 102. This angle, as denoted o in FIG. 1B, is the angle between the plane of plasma flood gun 106 and the direction of ion beam 102.

In some embodiments, more than two arc chambers 110 are configured in the same plane as the plasma flood gun. Angle ø shown in FIG. 1B is also the angle between the plane of the arc chambers 110 and the direction of ion beam 102.

In some embodiments, angle ø shown in FIG. 1B is 90 degrees. The more than two arc chambers 110 are oriented in a direction perpendicular to the direction of ion beam 102.

The more than two arc chambers 110, arranged in a straight line in FIG. 1A and 1B, are for the purpose of illustration only. In some embodiments, the arc chambers are arranged in a different configuration. Such configuration can be in a shape selected from a group consisting of a straight line, two parallel lines, a rectangle, a square, a triangle, an ellipse, a circle and a ring shape, or the like.

In some embodiments, such configuration depends on the shape of ion beam 102. For example, in some embodiments, ion beam 102 has a rectangle shape in a cross-section view, and the more than two arc chambers 110 can be arranged in one straight line, two double lines or in a rectangle shape. In some other embodiments, ion beam 102 is in a ring shape in a cross-section view, more than two arc chambers 110 are arranged in a shape such as a triangle, a square, an ellipse, a circle or any other suitable geometry.

In some embodiments, the more than two arc chambers 110 are arranged in a straight line, and ion beam 102 passes along a direction of such a straight line, or along a direction perpendicular to such a straight line.

In the case of any other shape except a straight line, ion beam 102 passes through a space between more than two zones of electrons released from arc chambers 110. In some embodiments, the more than two arc chambers are so arranged that ion beam 102 passes through the middle of the shape in which arc chambers 110 are configured. For example, in some embodiments, arc chambers 110 are arranged in a regular shape such as a triangle, a square, an ellipse and a circle, ion beam 102 passes through the middle of such geometry.

The exemplary ion implantation equipment systems and the arrangement of the arc chambers in FIG. 1A and 1B are for illustration purpose only. In addition to the planar configuration described above, the more than two arc chambers 110 can be arranged in any suitable three-dimensional configuration, in accordance with some embodiments of this disclosure.

FIG. 1C is an enlarged detail of an exemplary arc chamber 110 in the plasma flood gun in FIG. 1A and 1B, in accordance with some embodiments.

The exemplary arc chamber 110 comprises a chamber wall 118, a filament 116, a current source 112 electrically connected with filament 116, and a gas inlet 120 connected with arc chamber wall 118 to supply an inert gas into arc chamber 110. In some embodiments, a vacuum is applied inside arc chamber 110. In some embodiments, filament 116 is further biased at a negative potential through another power source 114, which is connected with emission current monitor 109 as shown in FIG. 1A and 1B. In some embodiments, arc chamber 110 is equipped with a cooling system. One exemplary cooling system uses continuous running water, running into and out of chamber wall 118, on which a built-in cavity or housing exists.

Power sources 112 and 114 are batteries in some embodiments. In other embodiments, power sources 112, 114 are DC power supplies, which can include a rectifier for converting alternating current to direct current, and a transformer. The voltages are in the range from 1-50 V. For example, in some embodiments, power source 112 provides 80 Amps of current and 3 volts of voltage, and power source 114 provides 10 Amps of current and 20 volts of voltage. In some embodiments, the maximum output of power source 112 for filament 116 is 800 W at 10 volts of DC voltage and 120 Amps of current. In some embodiments, the maximum output of power source 114 for arc is at 50 volts of DC voltage and 40 Amps of current.

In some embodiments, filament 116 is a metallic material. Filament 116 is tungsten, aluminum, molybdenum, or any other suitable metal or metal alloys. Filament 116 emits primary electrons when it is electrically heated by current source 112. In FIG. 1C, a negative sign in a circle stands for primary electrons. Primary electrons from such thermionic emission are accelerated by negative potential supplied by power source 114.

From gas inlet 120, an inert gas is introduced into the arc chamber 110 according to some embodiments. A noble gas having low ionization potential can be used. For example, xenon (Xe) is used in some embodiments. Xenon gas molecules collide with accelerated primary electrons inside arc chamber 110. A plasma flood comprising secondary electrons is then generated. As understood in the art, secondary electrons are electrons generated from ionized species under another primary irradiation source. In this illustrative example, the primary electrons generated from the filaments are the primary irradiation source. Xenon gases are ionized by the primary electrons. The electrons knocked off from xenon atoms are secondary electrons.

In some embodiments, primary electrons having low energy are released from the arc chambers into the ion beam in respective zones adjacent to a semiconductor wafer.

In one side of chamber wall 118, there is at least one aperture. The plasma flood comprising secondary electrons are released from the aperture, into ion beam 102 in the respective zones adjacent to semiconductor wafer 104, as shown in FIG. 1A and lB.

FIG. 2A-2E illustrate exemplary configurations of more than two arc chambers with different arrangements and shapes, with respect to an ion beam, in accordance with some embodiments. In each of these schematic drawings, for the purpose of illustration, more than two arc chambers 110 are arranged in one plane, which is perpendicular to the direction of ion beam 102. The "+" signs stand for positively charged ions in ion beam 102. The "−" signs represent electrons released arc chamber 110. The number of arc chambers 102 can be any number higher than two, and is not limited to those shown in FIG. 2A-2E. The more than two arc chambers 110 are interconnected through a housing or interconnected structure 210. interconnected structure 210 is connected with the cage 108 of the flood plasma gun apparatus, which is connected with an emission current monitor 109 and also grounded, as illustrated in FIG. 1A and lB. In some embodiments, interconnected structure 210 is a part of cage 108.

Figure 2B:
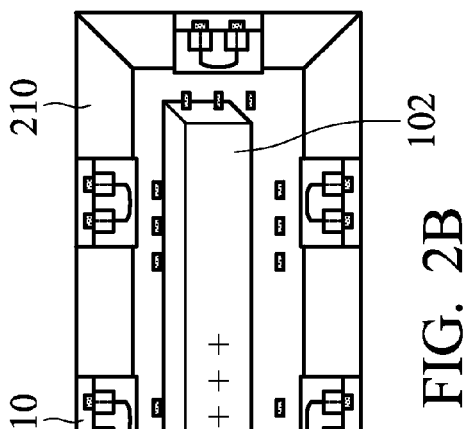
FIG. 2A-2E illustrate exemplary configurations of the more than two arc chambers with different combination of arrangements and shapes, with respect to an ion beam, in accordance with some embodiments.
Figure 2C:
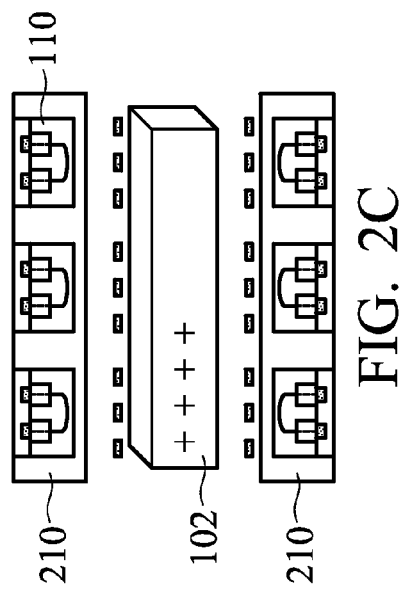
Figure 2A:
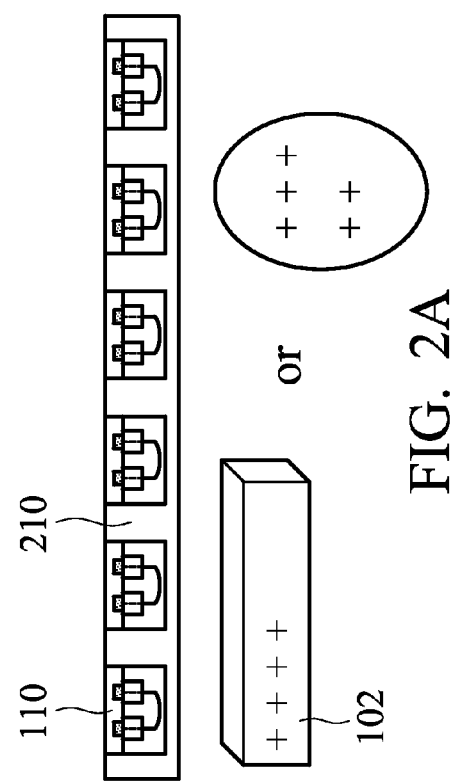

As illustrated in FIG. 2A, in some embodiments, ion beam 102 is in the shape of a rectangle or an ellipse in a cross-section view, and the more than two arc chambers 110 are arranged in a straight line. The number of arc chambers 102 is not limited to that shown in FIG. 2A, and is any number higher than two. In some embodiments, the ion beam 102 is in a spot shape or ellipse shape, and the number of arc chambers 102 is higher than two. For example, in some embodiments, three or more arc chambers 102 are needed for a large-sized ion beam.

As illustrated in FIG. 2B, in some embodiments, ion beam 102 is in the shape of a rectangle in a cross-section view, and more than two arc chambers 110 are also arranged in a rectangular shape in housing 210. Ion beam 102 passes through the enclosing space among arc chambers 110. Electrons released from each of arc chambers 110 are directed into ion beam 102 in a respective zone adjacent to semiconductor wafer 104 as described in FIG. 1B above. In some embodiments, ion beam 102 passes through the space among arc chambers 110 in the middle portion symmetrically.

As illustrated in FIG. 2C, in some embodiments, ion beam 102 is in the shape of a rectangle in a cross-section view, and more than two arc chambers 110 are arranged in a pair of parallel straight lines in housing 210. Ion beam 102 passes through the space between such two straight lines in the normal direction. Electrons released from each of arc chambers 110 are directed to ion beam 102 in a respective zone adjacent to semiconductor wafer 104 as described in FIG. 1B above.

Figure 2E:
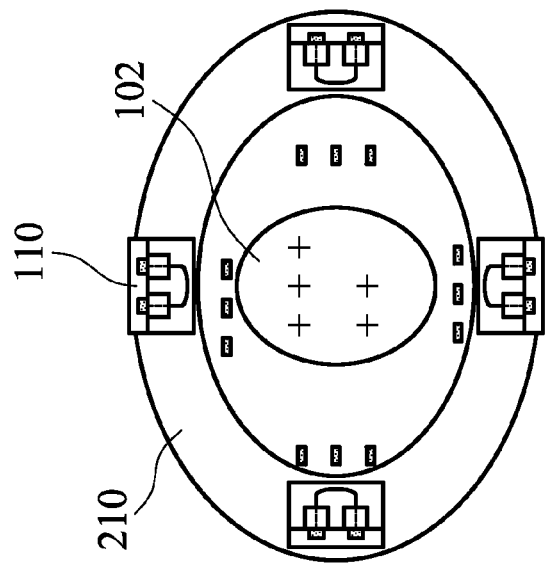
Figure 2D:
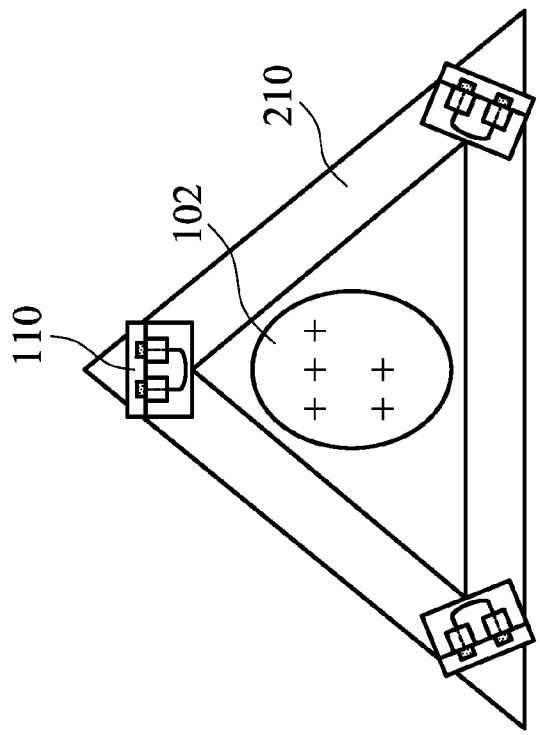

As illustrated in FIG. 2D, in some embodiments, ion beam 102 is in the shape of an ellipse in a cross-section view, and the more than two arc chambers 110 are arranged in a triangle configuration in housing 210. Ion beam 102 passes through the enclosing space among more than two arc chambers 110. Electrons released from each of arc chambers 110 are directed to ion beam 102 in a respective zone adjacent to semiconductor wafer 104 as described in FIG. 1B above. In some embodiments, ion beam 102 passes though the centroid of the triangular space among arc chambers 110.

As illustrated in FIG. 2E, in some embodiments, ion beam 102 is in the shape of an ellipse in a cross-section view, and more than two arc chambers 110 are also arranged in an ellipse, a circle or a ring geometry in housing 210. Ion beam 102 passes through the enclosing space among more than two arc chambers 110. Electrons released from each of arc chambers 110 are directed to ion beam 102 in a respective zone adjacent to semiconductor wafer 104 as described in FIG. 1B above. In some embodiments, ion beam 102 passes through the centroid of the space among arc chambers 110. In FIG. 2E, the major axis of the cross section of ion beam 102 is aligned with the minor axis of the cross section of the ellipse of arc chambers. In another embodiment, the major axis of the cross section of ion beam 102 is aligned with the major axis of the cross section of the ellipse of arc chambers.

FIG. 3 is a flow chart diagram illustrating an ion implantation method comprising the steps of generating and releasing electrons from more than two arc chambers in a plasma flood gun apparatus.

In step 302, ion beam 102 is generated in an ion source, and directed toward a semiconductor wafer 104, as described above in FIG. 1A-1B.

In step 304, electrons are generated from more than two arc chambers 110 in a plasma flood gun apparatus, as described above in FIG. 1C. In some embodiments, the electrons are secondary electrons.

In step 306, electrons are released from at least one aperture on the wall of arc chamber, into ion beam 102 in respective zones adjacent to the semiconductor wafer, as described above in FIG. 1C. The electrons surround the cross section of ion beam 102.

The released electrons neutralize ion beam 102 in the zones adjacent to the semiconductor wafer, and a possible charge buildup on the wafer surface.

The disclosure provides an apparatus having a plasma flood gun comprising more than two arc chambers, an ion implantation equipment system and an ion implantation method to neutralize ion beam in respective zone adjacent to a semiconductor wafer, and a positive charge buildup on the wafer surface during ion implantation.

In some embodiments, the apparatus comprises a plasma flood gun, which comprises more than two arc chambers. Each arc chamber is configured to generate and release electrons into the ion beam in a respective zone adjacent to the semiconductor wafer. In some embodiments, the electrons released from arc chambers are secondary electrons.

In some embodiments, the more than two arc chambers in the apparatus are oriented in a direction parallel to the direction of the ion beam. The ion beam passes along the direction of the arc chambers.

In some other embodiments, the more than two arc chambers are oriented at an angle with respect to the direction of the ion beam. In some embodiments, this angle is 90 degree, for example.

In some embodiments, the more than two arc chambers are also arranged in a configuration selected from a group consisting of a straight line, two parallel lines, a rectangle, a square, a triangle, an ellipse, a circle and a ring shape. In some embodiments, the ion beam passes through a space between at least two respective zones having electrons released from the arc chambers.

In some embodiments, the ion beam has a rectangular shape in a cross-section view, and more than two arc chambers are configured in a pair of parallel straight lines, or in rectangular or a square shape.

In some embodiments, the ion beam has an ellipse shape in a cross-section view, and more than two arc chambers are configured in a shape of a triangle, an ellipse, a ring, a circle or any other suitable geometry.

In some embodiments, the more than two arc chambers are configured in any three-dimensional positional combinations of direction and geometry.

In some embodiments, an ion implantation equipment system comprises
an ion beam source; and
a plasma flood gun apparatus for neutralizing a positive charge buildup on a semiconductor wafer during a process of ion implantation using an ion beam. The plasma flood gun apparatus comprises:
more than two arc chambers, wherein each arc chamber is configured to generate and release secondary electrons into the ion beam in a respective zone adjacent to the semiconductor wafer.

In some embodiments, an ion implantation method comprises the steps of
generating an ion beam and directing the ion beam toward a semiconductor wafer;
generating secondary electrons from more than two arc chambers in a plasma flood gun apparatus; and
releasing the secondary electrons into the ion beam adjacent to the semiconductor wafer. The secondary electrons neutralize the ion beam adjacent to the semiconductor wafer, mitigate or eliminate the charge buildup on the semiconductor wafer.

Although the subject matter has been described in terms of exemplary embodiments, it is not limited thereto. Rather, the appended claims should be construed broadly, to include other variants and embodiments, which may be made by those skilled in the art.

What is claimed is:

1. An apparatus comprising:
a plasma flood gun for neutralizing a positive charge buildup on a semiconductor wafer during a process of ion implantation using an ion beam, the plasma flood gun comprising more than two arc chambers, wherein each arc chamber is configured to generate and release electrons directly into the ion beam in a respective zone adjacent to the semiconductor wafer.

2. The apparatus of claim 1, wherein the more than two arc chambers are oriented in a direction parallel to the direction of the ion beam.

3. The apparatus of claim 1, wherein the more than two arc chambers are oriented at an angle with respect to the direction of the ion beam.

4. The apparatus of claim 3, wherein the more than two arc chambers are oriented in a direction perpendicular to the direction of the ion beam.

5. The apparatus of claim 3, wherein the more than two arc chambers are arranged in a configuration selected from a group consisting of a straight line, two parallel lines, a rectangle, a square, a triangle and a ring shape.

6. The apparatus of claim 5, wherein the more than two arc chambers are oriented in a configuration so that the ion beam passes through a space between at least two respective zones having electrons released from the arc chambers.

7. The apparatus of claim 6, wherein the ion beam has a rectangular shape in a cross-section view, and the more than two arc chambers are configured in a rectangular or a square shape.

8. The apparatus of claim 6, wherein the ion beam has an ellipse shape in a cross-section view, and the more than two arc chambers are configured in a triangular or ring shape.

9. The apparatus of claim 1, wherein the at least one arc chamber in each of the more than two zones comprises a filament; a current supply source electrically connected with the filament; a gas inlet connected with the arc chamber to supply an inert gas into the arc chamber; and at least one aperture in one wall of the arc chamber.

10. The apparatus of claim 9, wherein the filament is configured to generate primary electrons, the primary electrons to be collided with the inert gas to generate secondary electrons which are released into the ion beam through the apertures.

11. An ion implantation equipment system, comprising:
an ion beam source; and
a plasma flood gun apparatus for neutralizing a positive charge buildup on a semiconductor wafer during a process of ion implantation using an ion beam, which comprises:
more than two arc chambers, wherein each arc chamber is configured to generate and release secondary electrons directly into the ion beam in a respective zone adjacent to the semiconductor wafer.

12. An ion implantation equipment system of claim 11, wherein the more than two arc chambers in the plasma flood gun apparatus are oriented at a direction parallel to the direction of the ion beam.

13. An ion implantation equipment system of claim 11, wherein the more than two arc chambers in the plasma flood gun apparatus are oriented at an angle to the direction of the ion beam.

14. An ion implantation equipment system of claim 13, wherein the more than two arc chambers in the plasma flood gun apparatus are oriented at a direction perpendicular to the direction of the ion beam.

15. An ion implantation equipment system of claim 13, wherein the more than two arc chambers in the plasma flood gun apparatus are oriented in a configuration selected from a group consisting of a straight line, two parallel lines, a rectangle, a square, a triangle and a ring shape.

16. An ion implantation equipment system of claim 15, wherein the more than two arc chambers in the plasma flood gun apparatus are oriented in a configuration so that the ion beam of a shape passes through the space between the more than two zones.

17. An ion implantation method, comprising the steps of
  generating an ion beam and directing the ion beam toward a semiconductor wafer;
  generating secondary electrons from more than two arc chambers in a plasma flood gun apparatus; and
  releasing the secondary electrons directly from each arc chamber into the ion beam in a respective zone adjacent to the semiconductor wafer.

18. An ion implantation method of claim 17, wherein the secondary electrons are released from the more than two arc chambers in such a configuration that the secondary electrons surround the cross section of the ion beam adjacent to the semiconductor wafer.

\* \* \* \* \*